United States Patent [19]

Raduchel et al.

[11] 3,962,218

[45] June 8, 1976

[54] NOVEL PROSTANOIC ACID DERIVATIVES AND PROCESSES FOR THE PREPARATION THEREOF

[75] Inventors: Bernd Raduchel; Werner Skuballa; Helmut Vorbruggen; Walter Elger; Wolfgang Losert; Olaf Loge, all of Berlin, Germany

[73] Assignee: Schering Aktiengesellschaft, Berlin & Bergkamen, Germany

[22] Filed: May 23, 1974

[21] Appl. No.: 472,738

[30] Foreign Application Priority Data

May 30, 1973 Germany............................ 2328132

[52] U.S. Cl......................... 260/240 R; 260/340.7; 260/340.9; 260/468 D
[51] Int. Cl.².............. C07C 177/00; C07D 317/12; C07D 317/50; C07D 319/04
[58] Field of Search.......... 260/340.7, 340.9, 240 R, 260/468 D

[56] References Cited
UNITED STATES PATENTS

| | | | |
|---|---|---|---|
| 3,639,463 | 2/1972 | Pike et al. | 260/468 D |
| 3,804,880 | 4/1974 | Bergstrom et al. | 260/468 D |
| 3,816,508 | 6/1974 | Just | 260/468 D |
| 3,842,118 | 10/1974 | Lincoln, Jr. | 260/468 D |
| 3,879,423 | 4/1975 | Kelly | 260/340.7 |

*Primary Examiner*—Allen B. Curtis
*Attorney, Agent, or Firm*—Millen, Raptes & White

[57] ABSTRACT

Prostaglandins of the formula

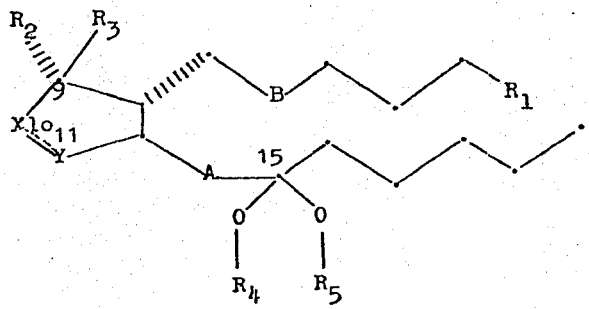

wherein $R_1$ is $HOCH_2$, —COOH, a salt thereof or an ester thereof; $R_2$ is OH; and $R_3$ is H or $R_2$ and $R_3$ collectively are = O. A is —$CH_2$—$CH_2$— or —(trans-)—CH=CH—, B is —$CH_2CH_2$—or —(cis-)—CH=CH— and $R_4$—O—O—$R_5$ is a ketal group, are superior in physiological activity to the corresponding 15-α-hydroxy-prostaglandins.

23 Claims, No Drawings

NOVEL PROSTANOIC ACID DERIVATIVES AND PROCESSES FOR THE PREPARATION THEREOF

BACKGROUND OF THE INVENTION

This invention relates to novel prostanoic acid derivatives and processes for the preparation thereof.

The novel prostanoic acid derivatives of this invention are 15-ketals of the naturally occurring prostaglandins and the synthetic analogs thereof. They exhibit a pharmacological spectrum of effectiveness which is similar to that of the natural prostaglandins.

Prostaglandins are $C_{20}$—unsaturated fatty acids having a wide variety of physiological effects (T. O. Oesterling et al, J. Pharmaceutical Sciences 61 (1972) 1861–1895), for example vasodilation, bronchodilation and inhibition of gastric acid secretion. Various natural prostaglandins, such as, for example, prostaglandin $E_2$ and prostaglandin $F_{2\alpha}$, are suitable for inducing abortion and initiation of labor.

The conventional prostaglandins are derivatives of prostanoic acid, which latter has the following formula:

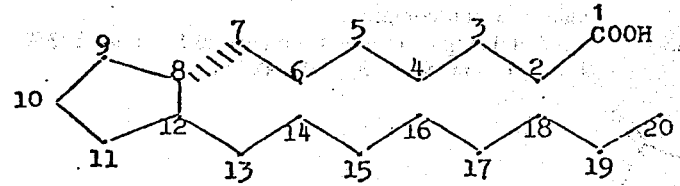

Examples of known prostaglandins (called PG hereinbelow) having the above basic prostanoic acid structure are:

PGE$_1$ ($\Delta^{13}$—9—keto—11$\alpha$, 15$\alpha$-diol),

PGF$_1\alpha$ ($\Delta^{13}$—9$\alpha$,11$\alpha$,15$\alpha$-triol) and

PGA$_1$ ($\Delta^{10,13}$—9—keto—15$\alpha$—ol).

PGE$_2$, PGF$_{2\alpha}$, PGA$_2$, like the compounds of the PG$_1$ series also have the above basic structure, except the linkage of the carbon atoms C-5 and C-6 is different. In the PG'$_2$ series, the C-5 and C-6 atoms are linked by a cis-double bond.

Thus, PG'F$_{2\alpha}$ is a $\Delta^{5,13}$—9$\alpha$,11$\alpha$,15$\alpha$-triol of the above basic structure.

PGE$_3$, PGF$_{3\alpha}$, and PGA$_3$ differ from the corresponding PG$_2$ compounds in that the C-17 and C-18 carbon atoms are linked by a cis-double bond. PGF$_{3\alpha}$ is a $\Delta^{5,13,17}$—9$\alpha$,11$\alpha$,15$\alpha$-triol of the above basic structure.

It is generally known that the physiological effects of the prostaglandins are only of a short duration in the mammal organism as well as in vitro. One reason for the rapid loss in effectiveness is seen in that a physiologically inactive metabolite is formed by the oxidation of the 15$\alpha$-hydroxy group. Thus, a 13,14-dihydro-15-dehydro derivative is formed, for example, from PGF$_{2\alpha}$, i.e., a $\Delta^5$—15—keto-9$\alpha$,11$\alpha$-diol of the above basic structure. (E. Granstroem and B. Samuelson, Eur. J. Biochem. 10 (1969) 411), which possesses the physiological effects typical for this class of substances only to a very greatly reduced extent.

Attempts have been made to inhibit the metabolizing of the 15-hydroxy group by the introduction of alkyl groups at the C-15 and/or C-16 atoms. (See German Unexamined Laid-Open Applications DOS 2,217,044; 2,121,980 and 2,221,301.) However, the synthesis of such alkylated prostaglandins is very expensive since the pure epimers are only obtained by time-consuming separation operations.

SUMMARY OF THE INVENTION

In a composition aspect, this invention relates to novel prostaglandins of the general Formula I

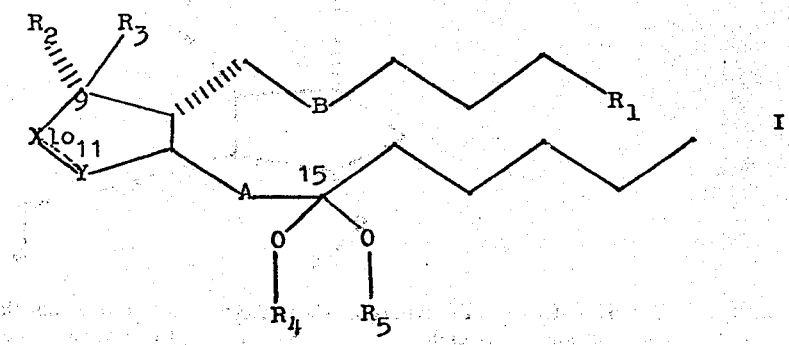

wherein $R_1$ is hydroxymethyl, carboxyl, alkoxycarbonyl of 1–8 carbon atoms in the alkoxy group, or —COO—CH$_2$—X—X, wherein X is a direct bond, carbonyl or carbonyloxy and Y is phenyl substituted by one or more of phenyl, alkoxy of 1–2 carbon atoms and halo; $R_2$ is hydroxy and $R_3$ is a hydrogen atom or $R_2$ and $R_3$ collectively are an oxygen atom; A is —CH$_2$—CH$_2$—or (trans)-CH=CH; B is —CH$_2$—CH$_2$- or (cis-)—CH=CH; $R_4$ and $R_5$ each are alkyl of 1–10 carbon atoms or collectively, a ring-forming divalent group of the formula —Z— wherein Z is a bridging alkylene having 2–3 carbon atoms in the carbon chain, and having a total of up to 23 carbon atoms or when alkylene contains at least 3 carbon atoms in the chain, alkylene substituted by hydroxy on a carbon atom other than one bonded to the ketal oxygen atom, e.g., —CH$_2$—CH$_2$—, —CH$_2$—CH$_2$—CH$_2$—, —CH$_2$—CH(C-H$_2$OH)—, —CH$_2$CHOH—CH$_2$—, —CH(Alk)—CH(Alk)—, —CH(Alk)—CH$_2$—CH(Alk)—, —CH$_2$—C(Alk)$_2$—CH$_2$—, —CH(Alk)—C(Alk)$_2$—CH(Alk), wherein Alk in each instance is straight-chain or branched alkyl of 1-5 carbon atoms, or a divalent aromatic or cycloalkyl group, e.g.,

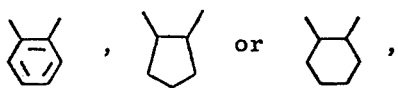

X=Y is

or when $R_2$ and $R_3$ collectively are =O, X=Y is

or HC=CH; and, when $R_1$ is carboxyl, physiologically acceptable salts with physiologically compatible bases.

In another composition aspect, this invention relates to novel intermediates for the production thereof.

DETAILED DISCUSSION

Of the compounds of Formula I, preferred are those wherein:

a. $R_1$ is —COOH, —COO—Alk, wherein Alk is alkyl of 1-5 carbon atoms, especially —COOCH$_3$, or —COO—p—phenylphenacyl;
b. B is —(cis)—CH=CH—, especially those of (a);
c. $R_2$ is OH and $R_3$ is H, especially those of both (a) and (b);
d. X=Y is

especially those of each of (a), (b) and (c);
e. $R_4$ and $R_5$ collectively are —CH$_2$—CH$_2$—, —CH$_2$CH$_2$—CH$_2$—, —CH$_2$—CH(CH$_2$OH)—, —CH$_2$—CH(OH)—CH$_2$—, —CH(Alk)—CH(Alk)—, —CH(Alk)—CH$_2$—CH(Alk)—, —CH$_2$—C(Alk)$_2$—CH$_2$—or —CH(Alk)—C(Alk)$_2$—CH(Alk)—, wherein Alk is alkyl of 1-5 carbon atoms, preferably wherein Alk is CH$_3$, especially those wherein $R_4$ and $R_5$ are —CH$_2$—CH$_2$—, including each of (a), (b), (c) and (d);
f. A compound of each of (a), (b), (c), (d) and (e), wherein $R_1$ is —COOH, as a physiologically acceptable salt thereof, especially a tertiary amine salt, e.g., triethylamine salt.

Suitable physiologically compatible bases for the salt formation are, for example, alkali metal hydroxides, e.g., sodium or potassium hydroxide, alkaline earth hydroxides, e.g., calcium hydroxide, ammonia, amines, e.g., ethanolamine, diethanolamine, triethylamine, N-methylglucamine, morpholine and tris(hydroxymethyl)methylamine.

In a process aspect, this invention relates to a process for the production of prostaglandins of general Formula I, which comprises:

a. ketalizing a ketone of the general Formula II (See J. Am. Chem. Soc. 93, 1491, 1971)

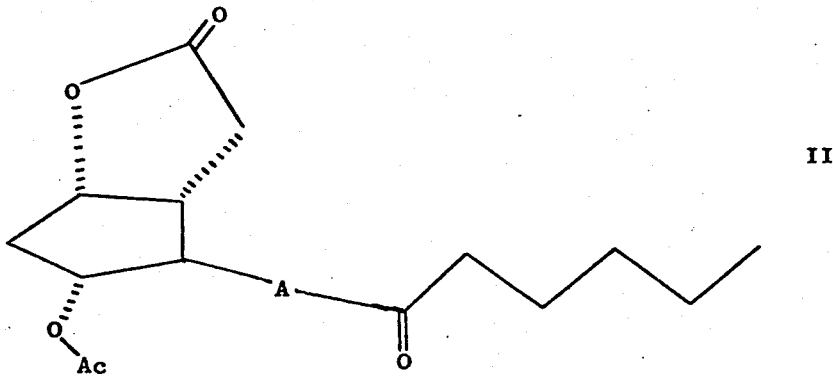

wherein A has the values given for Formula I and Ac is the acyl radical of an aliphatic or aromatic acid, with an alcohol of the general Formula IIIa, alkyl—OH(IIIa) wherein alkyl is alkyl of 1-10 carbon atoms or of the general Formula IIIb, HO—Z—OH (IIIb), wherein Z has the values given for Formula I; reducing the thus-obtained ketal of the general Formula IV

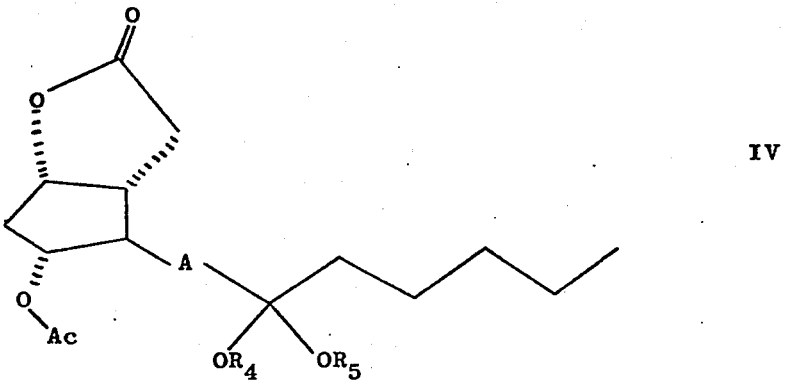

wherein A, R₄ and R₅ have the values given for Formula I and Ac has the values given for Formula II, in accordance with a simplified Corey synthesis corresponding to the U.S. Application of Bernd Raduechel et al. S.N. 472,737 filed May 23, 1974 (German Patent Application P 23 28 131.4) with diisobutylaluminum hydride or lithium tri-tert.-butoxy-aluminum hydride to the hemiacetal of the general Formula V oxidized and optionally dehydrated with elimination of the 11-hydroxy group, and/or the 5,6-double bond is hydrogenated, and optionally also a 1-carboxy compound is converted into a salt thereof with a physiologically compatible base; or b. ketalizing a ketone of the general Formula VII (see Eur. J. Biochem. 10, 411, 1969; Biochim. Biophys. Acta 218, 288, 1970)

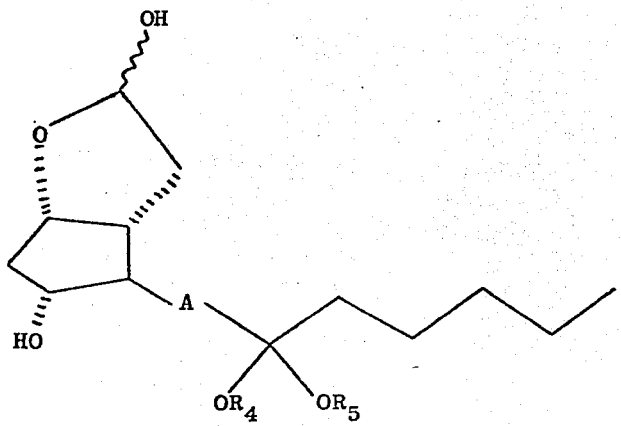

V

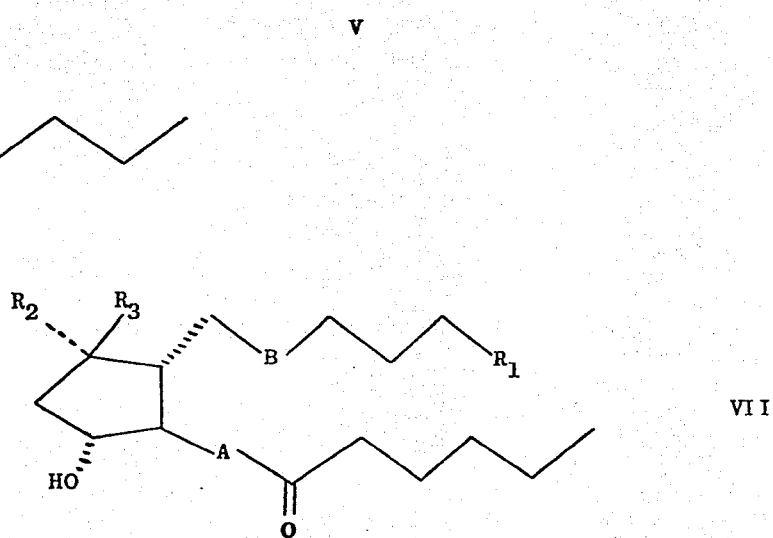

VII reacting the hemiacetal of general Formula V with a Wittig reagent of the general Formula VI wherein $R_1$, $R_2$, $R_3$, A and B have the values given for Formula I, with an alcohol of the general Formula IIIa or IIIb.

In addition to the compounds of general Formula I, this invention also relates to novel intermediates of general Formula IV and general Formula V.

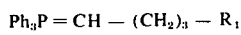

VI

In the first step for the production of the prostaglandins of general Formula I according to process (a), a ketone of the general Formula II is ketalized in a conventional manner. For example, the ketone is heated with an alcohol of general Formula IIIa or IIIb in the presence of an acidic catalyst and a diluent, with the water of reaction being separated to promote the ketalization. Suitable diluents are, for example, benzene, toluene, methylene chloride, ethylene chloride, chloroform and other water-immiscible inert organic liquids. Especially suitable as acidic catalysts are strong organic and inorganic acids, e.g., p-toluenesulfonic acid, sulfuric acid, hydrochloric acid and perchloric acid. Examples of polyol alcohols of general Formula IIIb are ethylene glycol, 1,3-propanediol, 2,2-dimethyl-1,3- wherein Ph is a phenyl group and $R_1$ has the values given in Formula I, to produce a compound of the general Formula Ia

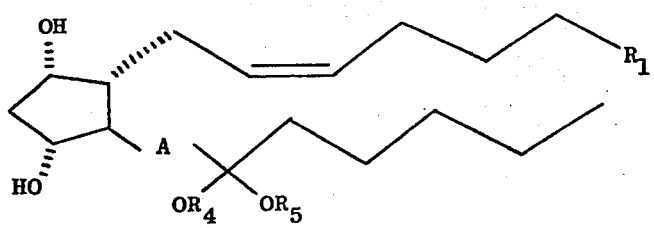

Ia and, depending on the desired value for $R_1$, $R_2$ and $R_3$ and B in the final product of general Formula I, optionally, in the thus-obtained compounds of Formula Ia, thereafter a 1-carboxy group is esterified and/or the 9—OH group, optionally after masking the 11-hydroxy group by silylation (Chem. Comm. (1972) 1120), is propanediol, 2,3-butanediol, pyrocatechol, 1,2-cyclopentanediol, 1,2-cyclohexanediol, glycerin. The alcohols of Formula IIIa are monohydric aliphatic alkanols of 1–10 carbon atoms. When ketalizing with monohydric alcohols, it is advantageous to add the corresponding trialkyl orthoformates and to conduct the reaction at room temperature, e.g., employing a large molar excess of the alcohol.

The ketals of general Formula IV obtained in the first step can be reduced to the hemiacetals of general Formula V with a solution of diisobutylaluminum hydride or lithium tri-tert.-butoxyaluminum hydride in an inert solvent at low temperatures. During this step, the ester group on the cyclopentane ring is concomitantly split off.

The reaction is conducted at low temperatures, preferably below 0° C., e.g., about −40° C. to −80° C. As is customary, the reduction is conducted in an inert solvent, e.g., hexane, toluene, glyme, diethyl ether or tetrahydrofuran.

The thus-produced hemiacetal of general Formula V is then reacted with a Wittig reagent of general Formula VI. The Wittig reagent can also be liberated during the reaction from 4-$R_1$-butyltriphenylphosphonium bromide in an aprotic solvent, e.g., dimethyl sulfoxide or dimethylformamide, with an anhydrous base. Suitable anhydrous bases are alkali-metal hydrides, e.g., sodium hydride, alkali-metal alkoxides, e.g., potassium tert.-butylate, and alkylalkali-metals, e.g., butyllithium. The reaction can be effected over a wide temperature range, e.g., 0° – 100° C., preferably 30° – 80° C.

The thus-obtained compounds of general Formula Ia can optionally be esterified, oxidized, dehydrated or hydrogenated subsequently according to conventional methods. The free acids can be converted into the salts thereof with physiologically compatible bases.

The esterification of the 1-carboxy compounds can be accomplished, depending on the significance of $R_1$ in the final product, either with ethereal diazoalkane solution or with a halogen compound of the general formula Hal — $CH_2$ — X — Y wherein Hal is a halogen atom, preferably bromine, and X and Y have the values given above, in the presence of an agent which splits off hydrogen halide.

Examples for suitable agents which split off hydrogen halide are silver oxide, sodium carbonate, potassium carbonate, sodium bicarbonate, potassium bicarbonate or amines, preferably tertiary amines, such as triethylamine, trimethylamine, tributylamine, trioctylamine and pyridine. The reaction with the halogen compound is conducted in an inert solvent, preferably in acetone, acetonitrile, dimethylacetamide, dimethylformamide or dimethyl sulfoxide, and at temperatures of −80° C. to +100° C., preferably at about room temperature.

The oxidation of the 9-hydroxy group can be effected with the aid of Collins reagent (Tetrahedron Letters 1968, 3363) in methylene chloride solution. In place of methylene chloride, it is also possible to use other solvents inert with respect to the oxidizing agent, e.g., chloroform, ethylene chloride and pyridine. Since the oxidation is to be accomplished selectively on the 9-hydroxy group, it is advantageous to protect the 11-hydroxy group before the oxidation, e.g., by selective silylation (J.C.S. Chem. Commun. 1972, 1120).

The dehydration of the 9-oxo compound with formation of a 10,11-double bond can be accomplished in the presence of dicyclohexylcarbodiimide and copper(II) chloride dihydrate in an inert solvent, preferably in an ether, e.g., diethyl ether, tetrahydrofuran, dioxane, dimethoxyethane, e.g., at temperatures of from 0° to 50° C.

The hydrogenation of the 5,6-double bond is in a hydrogen atmosphere in the presence of a noble metal catalyst. An example of a suitable catalyst is 10% palladium on charcoal. The hydrogenation is conducted at room temperature if no double bond is present in the 13-position, and at a low temperature, preferably at −80° to −10° C., if a 13,14-double bond is simultaneously present.

The ketalization of a ketone of general Formula VII according to process (b) can be conducted in a conventional manner with an alcohol of general Formula IIIa or IIIb. Ketones of general Formula VII can readily be obtained from the corresponding ketals of general Formula I with dilute mineral acids.

Ketones of general Formula II in which A is —CH=CH— are known from J. Amer. Chem. Soc. 92 (1970) 397. By hydrogenation of these unsaturated ketones with palladium/charcoal (10%) in ethyl acetate, the corresponding saturated compounds of general Formula II (A = —$CH_2$—$CH_2$—) can be obtained.

The novel compounds of general Formula I are valuable pharmacological agents, since, with essentially the same spectrum of effectiveness, they exhibit a substantially potentiated and particularly more prolonged activity than the corresponding 15-keto and 15-hydroxy-prostaglandins. Since the free 15-keto prostaglandins possess only a fraction of the original prostaglandin effects, the advantageous properties of the ketals could not be predicted. The novel compounds moreover exhibit the advantage that they are very easily accessible and can be obtained in the pure form without great technical expense.

For example, the compounds of Formula I exhibit good abortive activity in an in vivo test in which pregnant rats were treated with the novel prostaglandin ketals from the 4th to 7th day of pregnancy. The animals were sacrificed on the 9th day, and the uteri were examined for locations of implantation. In this test, the methyl ester of 9α,11α-dihydroxy-15,15-ethylenedioxy-5-cis,13-trans-prostadienoic acid, for example, was abortively effective in rats at 0.03 mg. dosage, whereas 1 mg. of PG $F_{2\alpha}$ was required to obtain the same effect.

Also, in the recordation of the isotonic uterus contractions on narcotized rats and on isolated rat uteri, it was found that compounds of Formula I are more effective than PG $F_{2\alpha}$, and their effects were of a longer duration.

Thus, for example, the methyl ester of 9α,11α-dihydroxy-15,15-ethylenedioxy-5-cis,13-trans-prostadienoic acid was found to be five times more effective in this test than PG $F_{2\alpha}$. The methyl ester of 11α-hydroxy-9-oxo-15,15-ethylenedioxy-5-cis,13-trans-prostadienoic acid possesses valuable differentiated properties. For example, in the uterus contraction test, the compound shows a somewhat lesser effect than PG $E_2$, whereas on the isolated guinea pig ileum the compound does not trigger any contractions even in 100 times stronger concentrations than PG $E_2$. This property is of significance in order to eliminate undesired side effects during fertility control.

The effective agents of this invention are to be utilized in conjunction with the auxiliary agents known and customary in galenic pharmacy, for example to manufacture preparations to trigger abortion or to induce labor. For this purpose, sterile aqueous solutions containing 0.01 – 10 μg./ml. of the active compound can be used as an intravenous infusion.

For the preparation of aqueous isotonic solutions, the acids and salts of general Formula I are especially suitable. To increase the solubility, alcohols can be added, such as ethanol and ethylene glycol.

The effective agents of this invention show pronounced bronchodilatory effects on the isolated rabbit trachea in vitro and strongly inhibit gastric acid secretion; they also have a regulatory effect in heart dysrhythmia. The ketals of the PG A and PG E series furthermore lower the blood pressure and have a diuretic effect.

If the active agents are to be utilized for these purposes, they can be converted into conventional forms adapted for inhalation or for oral or parenteral administration. For inhalation purposes, aerosol or spray solutions are suitably employed. Examples for oral application forms are tablets, dragees or capsules. For parenteral administration, sterile, injectable aqueous or oily solutions are utilized.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1 a. A mixture of 2.00 g. of 2-[3α-p-biphenyl-carbonyloxy-5α-hydroxy-2β-(3-oxo-trans-1-octen-1-yl)-cyclopent-1α-yl]-acetic acid γ-lactone, 30 mg. of p-toluenesulfonic acid, 5 ml. of ethylene glycol, and 150 ml of benzene was refluxed on a water trap for 3 hours. After cooling, the mixture was diluted with ether and shaken with sodium bicarbonate solution. The organic phase was dried over magnesium sulfate and evaporated under vacuum. The crystalline residue was recrystallized from hexane/methylene chloride, thus obtaining 1.95 g. of 2-[3α-p-biphenyl-carbonyloxy-5α-hydroxy-2β-(3,3-ethylenedioxy-trans-1-octen-1-yl)-cyclopent-1α-yl]-acetic acid γ-lactone, m.p. 128° C.

b. At −60° C., 19 ml. of a 20% solution of diisobutyl-aluminum hydride in hexane was added to a solution of 1.90 g. of 2-[3α-p-biphenyl-carbonyloxy-5α-hydroxy-2β-(3,3-ethylenedioxy-trans-1-octen-1-yl)-cyclopent-1α-yl]-acetic acid γ-lactone in 60 ml. of toluene. After 20 minutes, 3 ml. of isopropyl alcohol was added dropwise. The mixture was heated to room temperature, combined with 10 ml. of water, and agitated for 10 minutes. Subsequently, the mixture was diluted with ethyl acetate, the aqueous phase was separated, and the ethyl acetate layer was shaken with NaCl solution, dried over magnesium sulfate, and evaporated under vacuum. By filtration of the residue with ether over 40 g. of silica gel, p-phenylbenzyl alcohol was eluted. By elution with ether/dioxane (9 + 1), 1 g. of 2-[3α,5α-dihydroxy-2β-(3,3-ethylenedioxy-trans-1-octen-1-yl)-cyclopent-1α-yl]-acetaldehyde γ-hemiacetal was obtained as a colorless oil.

The thin-layer chromatogram of the product (ether/dioxane 2 + 1) showed a uniform spot having an $R_f$ value of 0.23.

c. 2.90 g. of 4-carboxybutyl-triphenylphosphonium bromide was dissolved in 12 ml. of dimethyl sulfoxide and combined with a solution of methanesulfonyl-methyl sodium obtained by dissolving 315 mg. of sodium hydride in 12.6 ml. of dimethyl sulfoxide at 70° C. After 15 minutes, a solution of 1 g. of 2-[3α,5α-dihydroxy-2β(3,3-ethylenedioxy-trans-1-octen-1-yl)-cyclopent-1α-yl]-acetaldehyde γ-hemiacetal in 15 ml. of dimethyl sulfoxide was added dropwise to the reaction mixture, and the latter was heated for 2 hours to 50° C. The mixture was then poured on 300 ml. of ice water and extracted with ethyl acetate. This extract was discarded. The aqueous solution was acidified with citric acid to ph 4–5 and extracted five times with respective 100 ml. of a mixture of hexane and ether (1 : 1). This extract was washed with NaCl solution, dried over magnesium sulfate, and evaporated under vacuum, thus obtaining a yellow oil (1.30 g.) purified by column chromatography on 100 g. of silica gel with the use of a mixture of ether and dioxane as eluent. Yield: 0.93 g. of 9α,11α-dihydroxy-15,15-ethylenedioxy-5-cis,13-trans-prostadienoic acid, m.p. 61° C.

The thin-layer chromatogram (ether/dioxane 2 + 1) showed a uniform spot having an $R_f$ value of 0.38.

EXAMPLE 2

An excess of an ethereal diazomethane solution was added to a solution of 100 mg. of 9α,11α-dihydroxy-15,15-ethylenedioxy-5-cis,13-trans-prostadienoic acid in 4 ml. of methylene chloride. After 5 minutes, the mixture was evaporated to dryness under vacuum, thus obtaining the methyl ester of 9α,11α-dihydroxy-15,15-ethylenedioxy-5-cis,13-trans-prostadienoic acid as a colorless oil. The thin-layer chromatogram (ether/dioxane 9 + 1) showed a uniform spot having an $R_f$ value of 0.20.

EXAMPLE 3

200 mg. of 9α,11α-dihydroxy-15,15-ethylenedioxy-5-cis,-13-trans-prostadienoic acid was mixed with 3 ml. of acetone and 56 mg. of triethylamine; after 10 minutes, the mixture was combined with 153 mg. of p-phenylphenacyl bromide and agitated overnight. The mixture was then diluted with water and repeatedly extracted with ether. The extract was shaken with NaCl solution, dried over magnesium sulfate, and evaporated to dryness under vacuum. The crude product was filtered over 10 g. of silica gel with ether/dioxane mixtures, thus obtaining 195 mg. of the p-phenylphenacyl ester of 9α,11α-dihydroxy-15,15-ethylenedioxy-5-cis,13-trans-prostadienoic acid, m.p. 79° C. (from hexane/methylene chloride). The thin-layer chromatogram (ether/dioxane 8 + 2) showed a uniform spot having an $R_f$ value of 0.35. By proceeding analogously to Example 3, but with use of p-chlorphenacylbromid,
p-bromphenacylbromid,
2,5-dimethoxyphenacylbromid,
p-phenylbenzylbromid, the corresponding prostaglandin esters are produced:

p-chlorphenacyl ester of 9α,11α-dihydroxy-15,15-ethylenedioxy-5-cis,13-trans-prostadienoic acid;
p-bromphenacyl ester of 9α,11α-dihydroxy-15,15-ethylenedioxy-5-cis,13-trans-prostadienoic acid;
2,5-dimethoxyphenacyl ester of 9α,11α-dihydroxy-15,15-ethylenedioxy-5-cis,13-trans-prostadienoic acid;
p-phenylbenzyl ester of 9α,11α-dihydroxy-15,15-ethylenedioxy-5-cis,13-trans-prostadienoic acid.

EXAMPLE 4

A mixture of 200 mg. of the methyl ester of 9α,11α-dihydroxy-15-oxo-5-cis,13-trans-prostadienoic acid, 200 mg. of 1,3-propanediol, 1 mg. of p-toluenesulfonic acid, and 20 ml. of benzene was refluxed for 2 hours on a water trap. The mixture was worked up as described in Example 1(a), thus obtaining 210 mg. of the methyl ester of 9α,11α-dihydroxy-15,15-propylenedioxy-5-cis,-13-trans-prostadienoic acid as an oil. The methyl ester of 9α,11α-dihydroxy-15-oxo-5-cis,13-trans-prostadienoic acid used as the starting material can be prepared as follows:

A mixture of 800 mg. of the methyl ester of 9α,11α-dihydroxy-15,15-ethylenedioxy-5-cis,13-trans-prostadienoic acid, 100 ml. of methylene chloride, and 10 ml. of 10% sulfuric acid was thoroughly agitated for 1 hour. After the acid had been separated, the mixture was washed neutral with water, dried over magnesium sulfate, and evaporated under vacuum, thus obtaining 700 mg. of the methyl ester of 9α,11α-dihydroxy-15-oxo-5-cis,13-trans-prostadienoic acid as an oil. The thin-layer chromatogram (ether/dioxane 8+2) showed a uniform spot having an $R_f$ value of 0.41.

By proceeding analogously to Example 4, but with the use of ethylene glycol, 2,2-dimethylene-1,3-propanediol, glycerin, pyrocatechol, 1,2-cyclohexanediol, or 1,2-cyclopentanediol in place of 1,3-propanediol, the corresponding prostaglandin ketals are produced:

methyl ester of 9α,11α-dihydroxy-15,15-ethylenedioxy-5-cis,13-trans-prostadienoic acid;
methyl ester of 9α,11α-dihydroxy-15,15-(2,2-dimethyl-1,3-propylenedioxy)-5-cis,13-trans-prostadienoic acid;
methyl ester of 9α,11α-dihydroxy-15,15-(2-hydroxy-1,3-propylenedioxy)-5-cis,13-trans-prostadienoic acid;
methyl ester of 9α,11α-dihydroxy-15,15-(1,2-phenylenedioxy)-5-cis,-13-trans-prostadienoic acid;
methyl ester of 9α,11α-dihydroxy-15,15-(1,2-cyclohexanylenedioxy)-5-cis,13-trans-prostadienoic acid; and
methyl ester of 9α,11α-dihydroxy-15,15-(1,2-cyclopentanylenedioxy)-5-cis,13-trans-prostadienoic acid.

EXAMPLE 5

A mixture of 300 mg. of the methyl ester of 9α,11α-dihydroxy-15,15-ethylenedioxy-5-cis,13-trans-prostadienoic acid, 30 mg. of 10% palladium on charcoal, and 25 ml. of ethyl acetate was agitated for 2 hours at −20° C. under a hydrogen atmosphere. The mixture was then filtered through a glass suction filter and the solution evaporated to dryness under vacuum. The thus-obtained oily methyl ester of 9α,11α-dihydroxy-15,15-ethylenedioxy-13-trans-prostenoic acid showed, in the IR spectrum, a band at 980 cm$^{-1}$ for a trans-double bond. The NMR spectrum indicated two olefinic protons.

EXAMPLE 6

At 0° C., 15 ml. of a 0.4-molar solution of Collins reagent (Tetrahedron Letters 1968, 3363) in methylene chloride was added dropwise under agitation to a solution of 604 mg. of the p-phenylphenacyl ester of 9α,11α-dihydroxy-15,15-ethylenedioxy-5-cis,13-trans-prostadienoic acid in 40 ml. of methylene chloride. After 15 minutes, the mixture was diluted with 200 ml. of ether and shaken successively with soda solution, 10% sulfuric acid, and water. Then, the mixture was dried over magnesium sulfate and evaporated under vacuum. The residue was chromatographed on 50 g. of silica gel, the elution being effected with ether/hexane mixtures and finally with ether. Yield: 310 mg. of the p-phenylphenacyl ester of 11α-hydroxy-9-oxo-15,15-ethylenedioxy-5-cis,13-trans-prostadienoic acid in the form of white crystals, m.p. 106° C. (from ether).

Analogously, the methyl ester of 11α-hydroxy-9-oxo-15,15-ethylenedioxy-5-cis,13-trans-prostadienoic acid is obtained as a colorless oil from the methyl ester of 9α,11α-dihydroxy-15,15-ethylenedioxy-5-cis,13-trans-prostadienoic acid by oxidation.

EXAMPLE 7

A mixture of 2.0 of 2-[3α-p-biphenyl-carbonyloxy-5α-hydroxy-2β-(3-oxo-trans-1-octen-1-yl)-cyclopent-1α-yl]-acetic acid γ-lactone, 4.50 g. of pyrocatechol, 30 mg. of p-toluene-sulfonic acid, and 400 ml. of benzene was refluxed for 24 hours with the use of a water trap. The mixture was then shaken several times with 5% sodium hydroxide solution solution and water, dried over magnesium sulfate, and evaporated under vacuum. Chromatography on 100 g. of silica gel with ether/hexane mixtures yielded 1.20 g. of pure 2-[3α-p-biphenyl-carbonyloxy-5α-hydroxy-2β-(3,3-phenylenedioxy-trans-1-octen-1-yl)-cyclopent-1α-yl]-acetic acid γ-lactone, m.p. 121° C. The γ-lactone was reduced with diisobutyl-aluminum hydride, analogously to Example 1(b), to the 2-[3α,5α-dihydroxy-2β-(3,3-phenylenedioxy-trans-1-octen-1-yl)-cyclopent-1α-yl]-acetaldehyde γ-hemiacetal; the hemiacetal was reacted with 4-carbonylbutyl-triphenylphosphonium bromide and sodium hydride in dimethylsulfoxide, analogously to Example 1(c), to obtain 9α,11α-dihydroxy-15,15-(1,2-phenylenedioxy)-5-cis,13-trans-prostadienoic acid, which latter was then converted, according to Example 2, into the methyl ester of 9α,11α-dihydroxy-15,15-(1,2-phenylenedioxy)-5-cis,13-trans-prostadienoic acid.

EXAMPLE 8

A mixture of 2.0 g. of 2-[3α-p-biphenyl-carbonyloxy-5α-hydroxy-2β-(3-oxo-trans-1-octen-1-yl)-cyclopent-1α-yl]-acetic acid γ-lactone, 40 ml. of methanol, and 0.01 ml. of concentrated sulfuric acid was allowed to stand for 2 hours at room temperature. Then, 5% sodium hydroxide solution was poured on the mixture and the latter extracted with ether. The ether layer was washed with water, dried with magnesium sulfate, and concentrated under vacuum, thus obtaining 1.80 g. of 2-[3α-p-biphenyl-carbonyloxy-5α-hydroxy-2α(3,3-dimethoxy-trans-1-octen-1-yl)-cyclopent-1α-yl]-acetic acid γ-lactone as an oil. The γ-lactone was reduced with diisobutylaluminum hydride, analogously to Example 1(b), to the 2-[3α,5α-dihydroxy-2β-(3,3-dimethoxy-trans-1-octen-1-yl)-cyclopent-1α-yl]-acetaldehyde γ-hemiacetal, and the hemiacetal was reacted with 4-carboxybutyl-triphenylphosphonium bromide and sodium hydride in dimethyl sulfoxide, analogously to Example 1(c), to 9α,11α-dihydroxy-15,15-dimethoxy-5-cis,13-trans-prostadienoic acid, which latter was then converted into the methyl ester in accordance with Example 2.

EXAMPLE 9 a. 3.7 g. of 2-[3α-p-biphenyl-carbonyloxy-5α-hydroxy-2β-(3-oxo-octan-1-yl)-cyclopent-1α-yl]-acetic acid γ-lactone, 50 mg. of p-toluenesulfonic acid, 8 ml. of ethylene glycol, and 200 ml. of benzene was refluxed for 3 hours on a water trap. After cooling, the mixture was diluted with ether, shaken with sodium bicarbonate solution, and the organic phase was dried over magnesium sulfate and evaporated under vacuum, thus obtaining 3.6 g. of 2-[3α-p-biphenyl-carbonyloxy-5α-hydroxy-2β-(3,3-ethylenedioxy-octan-1-yl)-cyclopent-1α-yl]-acetic acid γ-lactone. The thin-layer chromatogram (in ether) showed a uniform spot having an $R_f$ value of 0.46.

b. At −60° C., 20 ml. of a 20% solution of diisobutylaluminum hydride in hexane was added to a solution of 2 g. of 2-[3α-p-biphenyl-carbonyloxy-5α-hydroxy-2β-(3,3-ethylenedioxy-octan-1-yl)-cyclopent-1α-yl]-acetic acid γ-lactone in 60 ml. of toluene. After 20 minutes, 3 ml. of isopropyl alcohol was added dropwise to the reaction mixture, the latter was heated to room temperature, mixed with 10 ml. of water, and agitated for 10 minutes. The mixture was thereafter extracted with ethyl acetate and the ethyl acetate solution was shaken with NaCl solution, dried over magnesium sulfate, and evaporated to dryness under vacuum. The residue was filtered with ether over 45 g. of silica gel, the elution yielding first p-phenylbenzyl alcohol. With ether/dioxane (9 + 1), 1.05 g. of 2-[3α,5α-dihydroxy-2β-(3,3-ethylenedioxy-octan-1-yl)-cyclopent-1α-yl]-acetaldehyde γ-hemiacetal was obtained as a colorless oil. The thin-layer chromatogram (ether/dioxane 2 + 1) showed a uniform spot having an $R_f$ value of 0.23.

c. One gram of 2-[3α,5α-dihydroxy-2β-(3,3-ethylenedioxy-octan-1-yl)-cyclopent-1α-yl]-acetaldehyde γ-hemiacetal was converted into 9α,11α-dihydroxy-15,15-ethylenedioxy-5-cis-prostenoic acid in a Wittig reaction according to Example 1(c), thus obtaining 0.9 g. of this compound in the form of an oil. The thin-layer chromatogram (ether/dioxane 2 + 1 showed a uniform spot with an $R_f$ value of 0.57.

EXAMPLE 10

100 mg. of 9α,11α-dihydroxy-15,15-ethylenedioxy-5-cis-prostenoic acid was mixed with 1.5 ml. of acetone and 28 mg. of triethylamine; after 10 minutes, the mixture was combined with 77 mg. of p-phenylphenacyl bromide and agitated overnight. After dilution with water, the mixture was extracted with ether, the ether extract was shaken with NaCl solution, dried over magnesium sulfate, and evaporated under vacuum. The residue was filtered over 5 g. of silica gel with ether/dioxane mixtures, thus obtaining 98 mg. of the p-phenylphenacyl ester of 9α,11α-dihydroxy-15,15-ethylenedioxy-5-cis-prostenoic acid, m.p. 83° C. (from hexane/methylene chloride).

EXAMPLE 11

A solution of 200 mg. of 9α,11α-dihydroxy-15,15-ethylenedioxy-5-cis,13-trans-prostadienoic acid in 1 ml acetonitril was combined with 100 mg. of triethylamine. After 30 minutes, the mixture was evaporated to dryness under vacuum and the residue triturated with ether, thus producing 190 mg. of the triethylammonium salt of 9α,11α-dihydroxy-15,15-ethylenedioxy-5-cis,13-trans-prostadienoic acid as a white powder.

EXAMPLE 12

A mixture of 120 mg. of the p-phenylphenacyl ester of 11α-hydroxy-9-oxo-15,15-ethylenedioxy-5-cis,13-trans-prostadienoic acid, 350 mg. of dicyclohexylcarbodiimide, 40 mg. of copper(II) chloride dihydrate, 50 ml. of ether, and 2 mg. of pyridine was agitated at room temperature for 12 hours. Then, another 350 mg. of dicyclohexylcarbodiimide was added thereto and the mixture stirred for another 32 hours at room temperature. The mixture was then filtered and evaporated to dryness under vacuum. The residue was chromatographed on 15 g. of silica gel, eluted with ether while adding 1–3% dioxane, and the thus-obtained product was the p-phenylphenacyl ester of 9-oxo-15,15-ethylenedioxy-5,10-cis,13-trans-prostatrienoic acid.

EXAMPLE 13

A mixture of 5 g. of 2-[3α-p-biphenyl-carbonyloxy-5α-hydroxy-2β-(3-oxo-trans-1-octen-1-yl)-cyclopent-1α-yl]-acetic acid γ-lactone, 100 ml. of chloroform, 100 ml. of methanol, 50 ml. of trimethyl orthoformate, and $5.10^{-3}$ ml. of concentrated hydrochloric acid was allowed to stand overnight at room temperature, then combined with aqueous sodium bicarbonate solution, and extracted with ether. The extract was washed with brine, dried over magnesium sulfate, and evaporated under vacuum. The oily residue was chromatographed on 130 g. of silica gel with hexane/ether (7 + 3) mixture, thus obtaining 3.85 g. of 2-[3α-p-biphenylcarbonyloxy-5α-hydroxy-2β-(3,3-dimethoxy-trans-1-octen-1-yl)-cyclopent-1α-yl]-acetic acid γ-lactone as a colorless oil. The γ-lactone was reduced with diisobutylaluminum hydride, analogously to Example 1(b), to the 2-[3α,5α-dihydroxy-2β-(3,3-dimethoxy-trans-1-octen-1-yl)-cyclopent-1α-yl]-acetaldehyde γ-hemiacetal; the hemiacetal was reacted with 4-carboxybutyl-triphenyl-phosphonium bromide and sodium hydride in dimethyl sulfoxide analogously to Example 1(c) to 9α,11α-dihydroxy-15,15-dimethoxy-5-cis,13-trans-prostadienoic acid, which was then converted into the methyl ester thereof in accordance with Example 2.

The same compound is produced by the following process:

A mixture of 210 mg. of the methyl ester of 9α,11α-dihydroxy-15-oxo-5-cis,13-trans-prostadienoic acid (see Example 4), 4 ml. of chloroform, 4 ml. of methanol, 2 ml. of trimethyl orthoformate, and $2.10^{-4}$ ml. of concentrated hydrochloric acid was allowed to stand overnight at room temperature, then mixed with a few drops of triethylamine, and the solvent mixture was evaporated under vacuum. The residue was chromatographed on 10 g. of silica gel. With ether/2% dioxane, 68 mg. of the methyl ester of 9α,11α-dihydroxy-15,15-dimethoxy-5-cis,13-trans-prostadienoic acid was obtained as a colorless oil. TLC (ether/dioxane 9 + 1), $R_f$ value: 0.45.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A prostaglandin of the formula

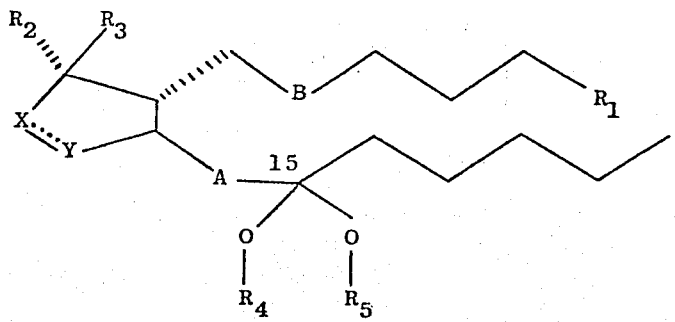

wherein $R_1$ is hydroxymethyl, carboxyl, alkoxycarbonyl of 1–8 carbon atoms in the alkoxy group, of —COO—$CH_2$—X—Y wherein X is a direct bond, carbonyl or carbonyloxy group and Y is phenyl substituted by phenyl, by alkoxy of 1–2 carbon atoms, or halo; $R_2$ is hydroxy and $R_3$ is a hydrogen atom or $R_2$ and $R_3$ collectively are an oxygen atom; A is (trans)—CH=CH—, B is —$CH_2$—$CH_2$ or (cis)—CH=CH—, $R_4$ and $R_5$ collectively are a ring-forming divalent group of the formula —Z— wherein Z is alkylene having 2–3 carbon atoms in the carbon chain and having a total of up to 23 carbon atoms or when alkylene contains at least 3 carbon atoms in the chain, alkylene substituted by hydroxy on a carbon atom other than one bonded to the ketal oxygen atom, or

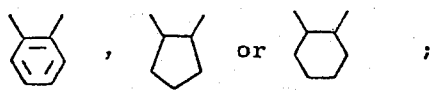

X=Y is

or when $R_2$ and $R_3$ collectively are an oxygen atom,

or HC=CH; and when $R_1$ is carboxyl, physiologically acceptable salts with a base.

2. A compound of claim 1 wherein $R_1$ is —COOH or a physiologically acceptable salt thereof, or —COO—Alk wherein Alk is alkyl of 1–5 carbon atoms.

3. A compound of claim 1 wherein B is —(cis-)—CH=CH—.

4. A compound of claim 1 wherein $R_2$ is OH and $R_3$ is H.

5. A compound of claim 1 wherein X=Y is

6. A compound of claim 1 wherein $R_4$ and $R_5$ collectively are —$CH_2$—$CH_2$—, —$CH_2$—$CH_2$—$CH_2$—, —$CH_2$—CH($CH_2$OH)—, —$CH_2$—CH(OH)—$CH_2$—, —CH(Alk)—CH(Alk)—, —CH(Alk)—$CH_2$—CH(Alk)—, —$CH_2$—C(Alk)$_2$—$CH_2$— or —CH(Alk)—C(Alk)$_2$—CH(Alk)—, wherein Alk is alkyl of 1–5 carbon atoms.

7. A compound of claim 6 wherein Alk is $CH_3$.

8. A compound of claim 1 wherein $R_1$ is —COOH or a physiologically acceptable salt thereof, or —COO—Alk wherein Alk is alkyl of 1–5 carbon atoms, wherein B is —(cis)—CH=CH—, wherein $R_2$ is OH and $R_3$ is H, wherein X=Y is

and wherein $R_4$ and $R_5$ collectively are —$CH_2$—$CH_2$—, —$CH_2CH_2$—$CH_2$—, —$CH_2$—CH($CH_2$OH)—, —$CH_2$—CH(OH)—$CH_2$—, —CH(Alk)—CH(Alk)—, —CH(Alk)—$CH_2$—CH(Alk)—, —$CH_2$—C(Alk)$_2$—$CH_2$— or —CH(Alk)—C(Alk)$_2$—CH(Alk)—, wherein Alk is alkyl of 1–5 carbon atoms.

9. A compound of claim 1, 9α,11α-dihydroxy-15,15-ethylenedioxy-5-cis,13-trans-prostadienoic acid.

10. A compound of claim 1, methyl ester of 9α,11α-dihydroxy-15,15-ethylenedioxy-5-cis,13-trans-prostadienoic acid.

11. A compound of claim 1, p-phenylphenacyl ester of 9α,11α-dihydroxy-15,15-ethylenedioxy-5-cis,13-trans-prostadienoic acid.

12. A compound of claim 1, methyl ester of 9α,11α-dihydroxy-15,15-propylenedioxy-5-cis,13-trans-prostadienoic acid.

13. A compound of claim 1, methyl ester of 9α,11α-dihydroxy-15,15-(2,2-dimethyl-1,3-propylenedioxy)-5-cis,13-trans-prostadienoic acid.

14. A compound of claim 1, methyl ester of 9α,11α-dihydroxy-15,15-(2-hydroxy-1,3-propylenedioxy)-5-cis,13-trans-prostadienoic acid.

15. A compound of claim 1, methyl ester of 9α,11α-dihydroxy-15,15-(1,2-phenylendioxy)-5-cis,13-trans-prostadienoic acid.

16. A compound of claim 1, methyl ester of 9α,11α-dihydroxy-15,15-(1,2-cyclohexanylenedioxy)-5-cis,13-trans-prostadienoic acid.

17. A compound of claim 1, methyl ester of 9α,11α-dihydroxy-15,15-(1,2-cyclopentanylenedioxy)-5-cis,13-trans-prostadienoic acid.

18. A compound of claim 1, methyl ester of 9α,11α-dihydroxy-15,15-ethylenedioxy-13-trans-prostenoic acid.

19. A compound of claim 1, p-phenylphenacyl ester of 11α-hydroxy-9-oxo-15,15-ethylenedioxy-5-cis,13-trans-prostadienoic acid.

20. A compound of claim 1, triethylammonium salt of 9α,11α-dihydroxy-15,15-ethylenedioxy-5-cis,13-trans-prostadienoic acid.

21. A compound of claim 1, p-phenylphenacyl ester of 9-oxo-15,15-ethylenedioxy-5,10-cis,13-trans-prostatrienoic acid.

22. A compound of claim 1, methyl ester of 11α-hydroxy-9-oxo-15,15-ethylenedioxy-5-cis,13-trans-prostadienoic acid.

23. A process for the production of prostaglandins of claim 1 which comprises the steps of:

a. ketalizing a ketone of the formula

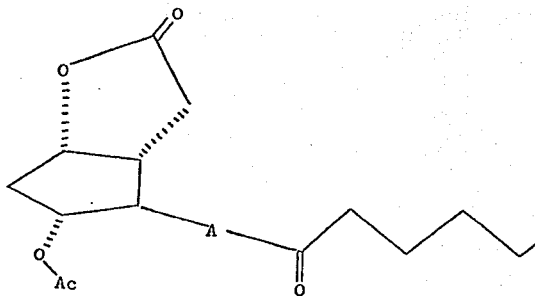

wherein Ac is an acyl radical of an aliphatic or aromatic acid, with an alcohol of the formula HO-Z-OH, wherein Z is alkylene having 2–3 carbon atoms in the chain and having a total of up to 23 carbon atoms or when alkylene contains at least 3 carbon atoms in the chain, alkylene substituted by hydroxy on a carbon atom other than one bonded to the ketal oxygen atom, or

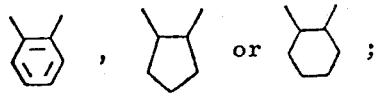

b. reducing the thus-obtained ketal of the formula

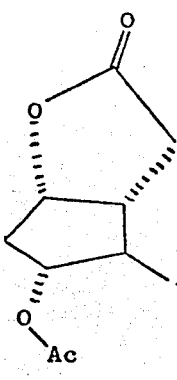

with diisobutylaluminum hydride or lithium tri-tert.-butoxyaluminum hydride; and c. reacting the thus-produced hemiacetal of the formula

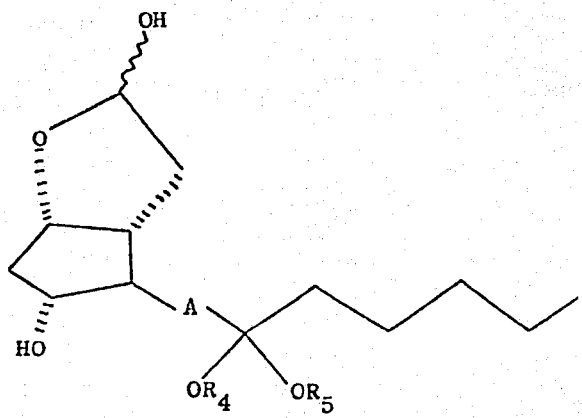

with a Wittig reagent of the formula $$Ph_3P = CH - (CH_2)_3 - R_1$$

wherein Ph is phenyl to produce a compound of the formula

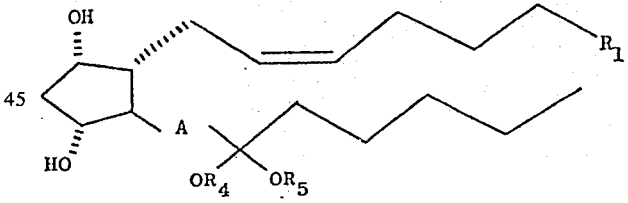

wherein $R_1$, $R_4$, $R_5$ and A have the values given in claim 1.

* * * * *